United States Patent [19]

Aronow

[11] 4,155,964
[45] May 22, 1979

[54] METHOD FOR PRODUCING SEMI-FINISHED PROSTHETIC DENTAL PREFORMS

[75] Inventor: Martin L. Aronow, Westbury, N.Y.

[73] Assignee: Sterndent Corporation, Old Greenwich, Conn.

[21] Appl. No.: 795,930

[22] Filed: May 11, 1977

[51] Int. Cl.² ............................ B29C 5/04; B28B 1/20
[52] U.S. Cl. ......................................... 264/13; 264/19; 264/69; 264/102; 264/250; 264/255; 264/334
[58] Field of Search ........................... 264/16–20, 264/13, 62, 63, 65, 310, 250, 255, 101, 102, 69, 334; 106/35, 39.5, 45, 46; 260/23 H, 42.52, 998.11; 427/2, 294, 350, 376 A

[56] References Cited

U.S. PATENT DOCUMENTS

| | | | |
|---|---|---|---|
| 1,896,123 | 2/1933 | Schweitzer | 264/19 |
| 2,000,285 | 5/1935 | Hoffman | 106/35 |
| 2,251,454 | 8/1941 | Jeffery | 264/5 |
| 2,317,103 | 4/1943 | Meier | 264/19 |
| 2,334,319 | 11/1943 | Erdle | 106/45 R |
| 2,368,816 | 2/1945 | Felcher | 264/19 |
| 2,463,551 | 3/1949 | Myerson et al. | 427/294 |
| 2,550,938 | 5/1951 | Raber | 264/19 |
| 2,597,469 | 5/1952 | Gatzka | 264/19 |
| 2,775,566 | 12/1956 | Crowley | 264/63 |
| 2,847,314 | 8/1958 | Fisher | 264/63 |
| 2,939,199 | 6/1960 | Strivens | 264/101 |
| 3,238,048 | 3/1966 | Somers | 264/63 |
| 3,238,049 | 3/1966 | Somers | 264/63 |
| 3,418,408 | 12/1968 | Emmel et al. | 264/334 |
| 3,635,759 | 1/1972 | Howatt | 427/376 A |
| 3,837,825 | 9/1974 | Loxley | 264/65 |
| 4,081,575 | 3/1978 | Spirig | 427/350 |

FOREIGN PATENT DOCUMENTS 366930  6/1973  U.S.S.R. ..................... 264/102

Primary Examiner—Willard E. Hoag
Attorney, Agent, or Firm—Pennie & Edmonds

[57] ABSTRACT

A method contemplated by the present invention for producing semi-finished prosthetic dental preforms essentially comprises the steps of repulverizing a dental porcelain mixture including a suitable binder by spray drying such dental porcelain molding the repulverized dental porcelain mixture in a die member having a cavity with a form generally complementary to that desired for the molded product, removing the molded product from the mold; and applying an outer coating of a suitable second dental porcelain to selected exterior surfaces of the molded product. The binder for the ceramic material comprises 10.5% to 8.5% ethylene vinyl acetate resin, 5.3% to 3.9% mineral seal oil and about 2.2% to 1.6% stearic acid.

4 Claims, 16 Drawing Figures

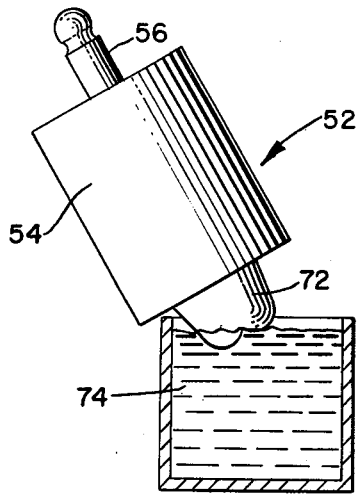
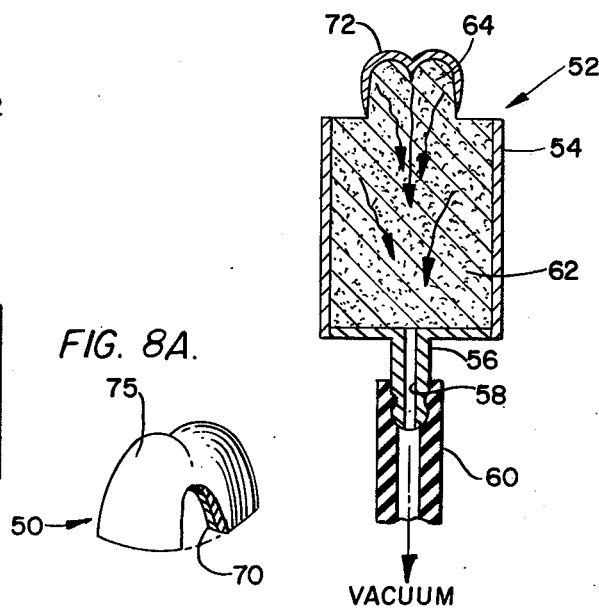
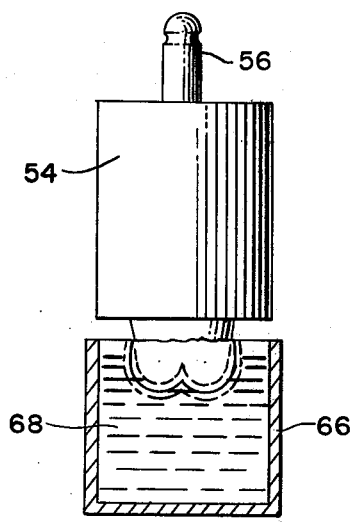
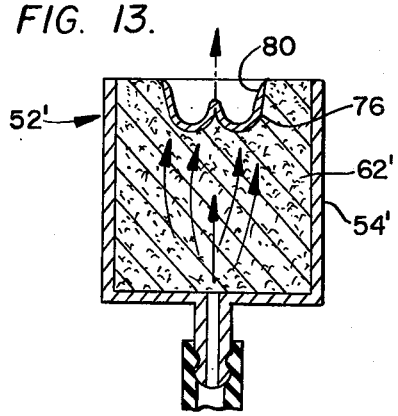
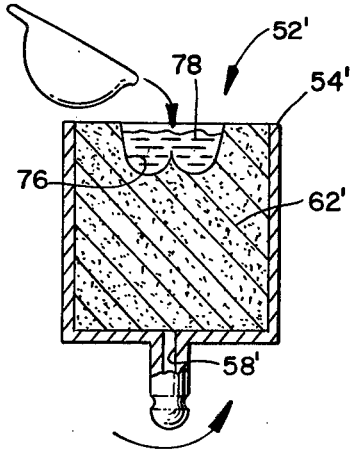
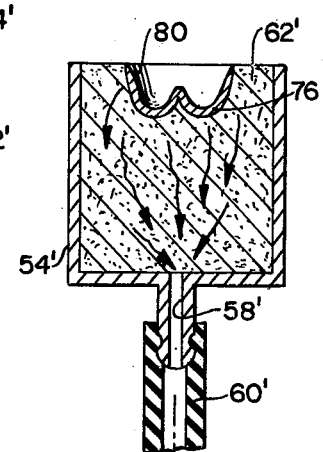
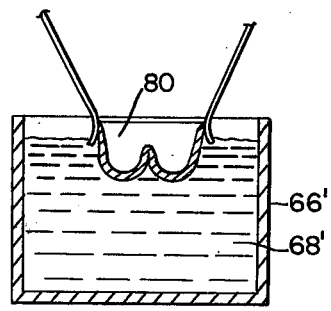

METHOD FOR PRODUCING SEMI-FINISHED PROSTHETIC DENTAL PREFORMS

BACKGROUND OF THE INVENTION

1. Field of the Invention

Generally speaking, the present invention pertains to the formation of prosthetic dental preforms. More specifically, it is directed to improved methods of producing semi-finished dental porcelain prosthetic crowns and the like.

2. Description of the Prior Art

It is customary practice in the dental field to produce artificial or prosthetic dental preforms, such as crowns and the like. Dental technicians and dentists will select a semi-finished tooth which generally meets the requirements of the dental patient and, thereafter, attempt to fit the preform on a member so as to become a part of a dental appliance, such as bridges and the like. Porcelain is added, as necessary, to achieve the desired shape and color.

The usual technique for producing these preforms can be generally characterized as comprising several rather lengthy steps involving many manual operations. Some of these steps involve building-up and sculpturing a prostheses by hand to simulate the replaced tooth in size, shape and color. It is pointed out that such technique, besides involving several tedious steps often requiring high level skills, also suffers from the shortcoming that it is time consuming. Apart from the foregoing drawbacks, such known technique is also economically limited insofar as only a few of the custom-made prostheses can be produced in any given period of time.

One known material used for producing semi-finished dental preforms employs a dental porcelain mixture including a binder compound which can subsequently be vitrified. In practice, porcelain is highly desirable as a material for prosthetic tooth components since it provides for extra hardness and improved aesthetics. Porcelain more satisfactorily withstands normal use and even abnormal use without failure or appreciable wear. It will be understood that failure of the prosthetic tooth component would cause unnecessary hardship to the patient. Owing, however, to the chemical and physical properties of such types of porcelain as is customarily used in this field, it has been determined from practice that such porcelain is a relatively difficult substance to work with, particularly from the dental standpoint of exactly reproducing numerous custom-made artificial prostheses. It should be pointed out that in the dental field the term dental porcelain is generally used to describe a low alumina ceramic mixture including binder before it is fired or vitrified. Once, however, the ceramic mixture is vitrified it then becomes what is generally regarded as porcelain material.

One known technique used for forming dental porcelain preforms utilizes an appropriate type of ceramic powder mix in conjunction with a suitable liquid binder which are thoroughly admixed into a paste. The paste is molded into the approximate form of a finished crown tooth, for instance, with allowances for porcelain shrinkage. Conventionally, body porcelain and incisal porcelain which go into forming the preform are suitably placed in appropriate locations in a flexible mold. Excess moisture is removed and the noted paste material is dried by heating at a temperature which is sufficiently high in magnitude to burn out or evaporate such excess moisture as well as set the binder material. In such usual process, the removed dried product is then baked or pre-fired to a hard concretious state but, however, is not vitrified. However, the binder leaves undesirable porosity and color.

Exemplary of other known approaches for manufacturing artificial tooth components are generally described in the following U.S. Pat. Nos.: 1,599,084, 1,868,425, 2,584,109, 2,317,103, 2,332,537, 2,333,833, 2,345,305, 2,368,816, 2,491,097, 2,514,076, 2,654,949, 2,703,435, 3,789,910, 3,766,650 and 3,621,576.

Other long recognized problems generally encountered in forming prosthetic dental porcelain preforms is the fact that the accuracy and uniformity of large quantities of molded products vary. Since the formation of accurately and uniformly produced semi-finished preforms varies known processes are rendered less than entirely successful. Also, it has been ordinarily experienced that a known method for forming porcelain preforms is not successful in terms of repeatability, as well as produces preforms which are lacking in sufficient strength for the intended purposes, inter alia, hand carving. Moreover, another significant disadvantage generally associated with heretofore known practices in this field is the fact that the labor costs attendant with the manufacture are relatively high.

Although it has been known to injection mold ceramic materials such as generally described in U.S. Pat. No. 2,964,245, such described process would be unsuitable for purposes of injection molding ceramic materials for dental preforms which have relatively small dimensions and desired color and translucency requirements.

Based upon the preceding considerations regarding the aforenoted contemporary approaches relating to the formation of semi-finished porcelain, prosthetic preforms, it is quite apparent that they are not as economically produced or as reliably consistent as could otherwise be obtained, since with ceramics it is extremely difficult to reliably obtain accurate and uniform preforms particularly whenever producing large numbers of such preforms on a commercial scale. Moreover, the strength of the preforms produced by such methods are inconsistent and, in general, not as high as could otherwise be produced. Additionally, the overall labor costs involved in producing dental preforms are disadvantageous since they are relatively high.

SUMMARY OF THE INVENTION

The present invention seeks to overcome the aforementioned difficulties typically encountered in the field of manufacturing by providing novel and improved methods for producing the same.

Broadly, in accordance with the invention, there is contemplated a method for producing semi-finished dental preforms which comprises the steps of repulverizing a dental porcelain mixture having a suitable binder therefor by spray drying the dental porcelain mixture, molding the repulverized dental porcelain mixture in a die member having a cavity with a form generally complementary to that desired for the molded product, removing the molded product from the mold and applying a suitable outer coating of a suitable second dental porcelain material to selected exterior surfaces of the molded product. In one embodiment of such method, the outer coating is of incisal or occlusal dental porcelain and applied by dipping the compacted and molded product into a thin slurry containing such dental porcelain material.

Another method contemplated is particularly adapted to form prosthetic tooth crowns and essentially comprises the steps of forming a protruding relatively hard porous material form into a shape which is generally similar to the exterior surface of the tooth crown envisioned taking into account the predetermined dental porcelain thicknesses and adjusting for the expected shrinkage of the dental porcelain material, applying a dental porcelain mixture on the hard porous molded form until a predetermined tooth crown thickness is achieved, applying at least reduced pressure with respect to ambient pressure to the porous material while the molded dental porcelain product is soft to effect evaporation of excess liquid binder and water solution during the drying of the dental porcelain thereby achieving an even, denser product free of bubbles or voids, removing the molded product from the cavity, and applying an amount of a suitable outer coating of a second dental porcelain material on selected exterior surfaces of the molded product.

Additionally, this invention embodies a method of producing semi-finished dental porcelain prosthetic preforms which comprise the steps of forming a cavity in a relatively hard porous mold material which has a configuration that is generally complementary to the exterior surface of the article which is to be molded, pouring a dental porcelain mixture having a suitable binder therefor into a hard porous mold material, moving the mold to ensure uniform and generally predetermined thickness of the dental porcelain in the cavity, pouring excess dental porcelain mixture from the cavity once the desired porcelain thickness is obtained, applying at least reduced pressure with respect to ambient to the porous material while the porcelain molded product is soft, to effect evaporation of excess liquid binder and water solution during drying of the dental porcelain thereby achieving an even denser product free from bubbles or voids, and applying an amount of a suitable outer coating of a second dental porcelain onto selected exterior surfaces of the molded product.

BRIEF DESCRIPTION OF THE DRAWINGS

The above, as well as other objects, features and advantages of the present invention shall be readily apparent upon a reading of a detailed description thereof when viewed in conjunction with the accompanying drawings, wherein the several views depict the sequence of operational steps involved and like reference numerals depict like structure throughout the several views.

FIG. 8 represents a diagrammatic view of a third method embodying the principles of the present invention wherein a molded porous form is dipped into a slurry comprising suitable occlusal or incisal dental porcelain material;

FIG. 8A represents a diagrammatic view of a prosthetic dental crown manufactured in accordance with the steps of the method depicted in FIG. 8;

FIG. 9 is a cross-sectional view illustrating a mold containing member being subject to a vacuuming step as envisioned by a third method embodying the principles of this invention;

FIG. 10 represents a diagrammatic view of a dipping step embraced by the third method of the present invention;

FIG. 11 represents a cross-sectional view diagrammatically illustrating a fourth method embodying the principles of the present invention wherein a slurry of dental porcelain is poured into a recess formed in a mold containing member;

FIG. 12 is a view depicting another sequential step in the fourth method of the present invention wherein a mold containing member is shown being subject to a vacuuming step;

FIG. 13 represents a diagrammatic view showing a removal step whereby the molded product is intended to be removed from the recess; and FIG. 14 represents a diagrammatic view illustrating a dipping step as is contemplated by the present embodiment to be preformed after the removing step shown in FIG. 13.

DETAILED DESCRIPTION

With initial reference to FIGS. 1 to 4, there is illustrated a selected sequence of operations as embodied by one method of this particular invention. Generally speaking, such method pertains to the formation of semi-finished prosthetic dental preforms 10 (FIG. 4A) which are essentially comprised of suitable dental porcelain materials. The present application generally describes a sequence of steps for producing dental porcelain preforms. It is to be understood that the term dental porcelain describes a ceramic mixture having a suitable binder therefor. It is pointed out that dental porcelain is different from that material which is customarily regarded as porcelain since the latter is not formed until the ceramic mixture has been fired or vitrified. Accordingly, in the parlance of the dental field the terminology dental porcelain is ordinarily used whenever referring to a pre-fired or vitrified ceramic mixture. As used herein the term "dental porcelain" encompasses the powder ceramic mixture having binder or liquid ceramic mixture having binder with any of the known necessary materials generally used in this field for the manufacture of such dental porcelain. As further used herein whenever porcelain is referred to in the context of firing or vitrification it denotes vitrified porcelain.

Figure 1:
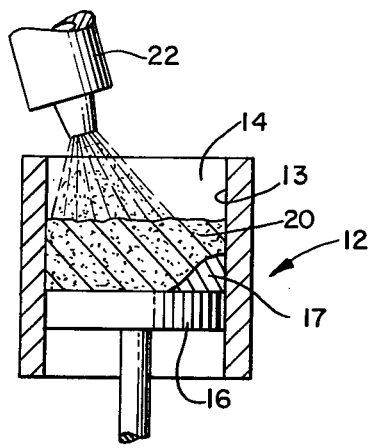
FIG. 1 is a diagrammatic view illustrating one step of a method embodying the principles of the present invention wherein repulverized dental porcelain and a suitable binder therefor are depicted being charged into a molded cavity.

Specifically referring to FIG. 1, there is depicted a die assembly 12 of the type which may be generally used in the formation of molded objects, especially dental porcelain prosthetic preforms. The die assembly 12 can be fabricated from any suitable metal or other material capable of withstanding the temperature and pressures employed in the present compression molding step to be described. It is pointed out that the die assembly 12 depicted should in no manner be interpreted as a limitation upon the method of forming semi-finished preforms. Rather, such a depiction is for purposes of illustration.

In general, the die assembly 12 may have side walls 13 which define a preform molding cavity 14. The cavity 14 may have any suitable size, shape and contour which is, preferably, at least partially complementary to the exterior shape of the semi-finished dental preform 10. A movable die platform member 16 operatively cooperates with the side walls 13, in standard fashion, to form the bottom wall of the cavity 14. Platform die member 16 is guided within and by the side walls 13 and is adapted to remain in the rest position during the steps of depositing spray dried dental porcelain having an appropriate binder therefor and compressing the deposited spray dried dental porcelain. The movable platform die member 16 may be of the type which can be raised from the positions shown in FIGS. 1 and 2 to that depicted in FIG. 3 by any suitable moving mechanism. As noted, the platform 16 has appropriately fastened thereto a molding member 17 which further acts to define the molded contours of preform 10. Other configurations for molding member 17 may, of course, be used consistent with conventional practice in this field.

Figure 2:
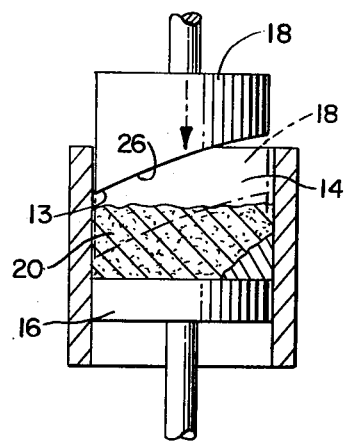
FIG. 2 is another diagrammatic view further illustrating one of the sequences of steps of this invention as being a molding step wherein the repulverized dental porcelain mixture with binder are subject to compression.

As perhaps more clearly shown in FIG. 2, the die assembly 12 is also comprised of a vertically reciprocal upper ram member 18. The upper ram 18 is arranged to be selectively moved into the cavity 14 as shown by the dotted lines in FIG. 2, for purposes presently described.

This particular method envisions a suitable dental porcelain powder mixture 20 having an appropriate binder of the type utilized for forming semi-finished prosthetic dental preforms, the constituents forming the dental porcelain are well known to those skilled in this art and further elaboration is not deemed necessary.

It is significant that this particular method employs a repulverized dental porcelain material for purposes presently mentioned. The repulverization is accomplished through conventional spray drying which is not shown, but is generally well known. The spray drying is performed to ensure repulverization of the dental porcelain mixture 20 including the binder. It has been determined that by utilizing spray dried dental porcelain material, such serves to advantageously facilitate an even compacter and, of course, denser semi-finished dental preform 10 than could otherwise be accomplished. Consequently, the dental preform 10 is much stronger. Also, the repulverized dental porcelain is easier to compress into the form desired.

Any suitable dispensing gun 22 may be employed for depositing the spray dried dental porcelain powder mixture 20 having a binder into the mold cavity 14 from the spray drying apparatus. Alternatively, the repulverized dental porcelain mixture with binder may be conveniently stored after a repulverizing step in a conventional fashion. Although a dispensing gun 22 may be used for purposes of charging the repulverized material into the cavity, other approaches for so filling the cavity may be appropriately applied. By virtue of the spray drying action and the use of the dispensing gun 22 the repulverized material 20 may be directed to the die cavity 14 in a single step. Selection of the proper spraying force can be appropriately selected in any known manner so as to prevent formation of clumps of material thereby ensuring original fineness. It will be seen from FIG. 1 that the spray dried dental porcelain mixture 20 including binder suitably fills cavity 14. At the conclusion of the foregoing charging step a compressing step may be performed in a manner to be presently described. It will be understood that when the binder is added to ceramic powder the spray drying is the means used to remove the solvent in the binder and distribute the binder uniformly with the ceramic powder. By repulverizing the dental porcelain greater cohesion occurs whenever a green compact member is formed as a result of pressure molding.

During the compressing step set forth in FIG. 2, it will be appreciated that the platform die member 16 may be suitably held in a stationary fashion to facilitate the compression necessary to form the molded or "green" compact member 24 (FIG. 3) whenever the upper ram 18 is downwardly moved during the compressing step. The movable upper ram 18 may have a contoured surface 26 which is formed for purposes of facilitating the formation of the size, shape and contour for the green compact member 24. Generally, the die assembly 12 is appropriately heated consistent with known practice in this field to a temperature sufficient to facilitate the formation of the molded compact member 24. Moreover, the ram member 18 applies a sufficient pressure to the material 20. Although not shown, such a compression step forms a flash which is suitably removed at the conclusion of the compressing step described above.

Figure 3:
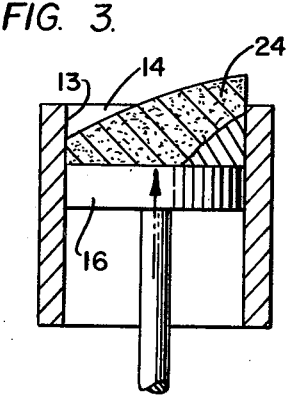
FIG. 3 is a diagrammatic view illustrating a removing step of a compacted molded green product from a die after the compression step depicted in FIG. 2.

To appropriately remove or displace the green compact member 24 from the cavity 14 the lower platform die member 16 is suitably lifted by means not shown and not forming an aspect of this invention. Accordingly, the molded member 24 is raised from the die assembly 12, as is depicted in FIG. 3. It will, of course, be understood that the upper vertical ram 18 has been suitably raised to avoid hindering removal of the compact member 24 from cavity 14.

Figure 4A:
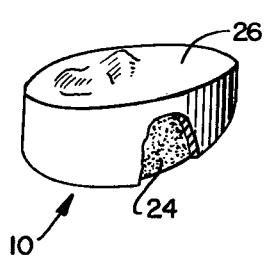
FIG. 4A represents a diagrammatic view of a prosthetic preform manufactured in accordance with the steps of the method depicted in FIGS. 1 to 4.
Figure 4:
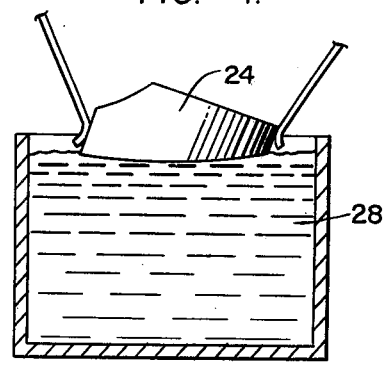
FIG. 4 is a diagrammatic view depicting another step which is in accordance with the principles of the present invention of a process wherein the compacted molded product is dipped into a porcelain slurry.

Upon completion of the compressing and removing steps, the molded member 24 is appropriately and selectively coated with an outer coating 26 of a second dental porcelain material 28 much as in the manner depicted in FIG. 4. For instance, such an outer coating may be comprised of incisal porcelain for the anterior teeth or occlusal porcelain for the posterior teeth. The outer coating is selected to provide the preform with desired color and translucency for better resembling natural teeth. Accordingly, such outer coating 26 provides for a better aesthetic appearance of the dental preform. Also, in this fashion, the dental preform can have the desired hardness, size, translucency and color. Towards this end, the molded member 24 may be suitably dipped, as by trays or the like, into a conventional slurry of so-called incisal or occlusal dental porcelain. It should be pointed out that in practice and as used throughout this application incisal and occlusal porcelain are comprised of the same materials. The difference in terminology refers to its location on the preform. The slurry comprises the ceramic mixture including the binder but in liquid form.

It will be appreciated that other suitable dental porcelain coating procedures are contemplated by the invention. Although dipping has been disclosed by the illustrated embodiment, the green compact member 24 may be coated through the application of other techniques including immersing, spraying or brushing procedures. It will be further appreciated that selected surface portions of the green compact member 24 are suitably coated with the necessary amount of incisal or occlusal dental porcelain in a standard manner nor forming a part of this invention. The dipping is performed to achieve the desired incisal or occlusal material thickness. Such desired thickness is obtained in a known manner through a repeated number of successive dipping and drying operations. Consequently, the desired outer dental porcelain coating 26 thickness is conventionally obtained. Usually, the incisal or occlusal porcelain has relatively harder characteristics than the compact member 24 and is added to areas for principally providing an aesthetic appearance by enabling the preform to have the desired translucency and color among other properties.

The applied outer coating of the incisal or occlusal dental porcelain is dried in any suitable fashion. Typically, the drying may take place at about 400° F. and then baked at a temperature of 1200° F. or over, but the coated compact member is not vitrified. Suitable drying apparatus is contemplated for performing the drying and baking functions. As aforementioned, the resulting semi-finished dental preform 10 made by following the foregoing sequence of steps may be appropriately fitted and mounted on a member so as to become part of a typical prosthetic appliance. Alternatively, the dried dental porcelain preform 10 may be sold generally in the form above described for well known purposes. In this embodiment as in the succeeding described embodiments, the conventional heating and baking steps are performed for a time sufficient to have the coated dental porcelain molded product formed into a preferably hard concretious state. Also, the invention contemplates that the preform can be subsequently vitrified.

Figure 5:
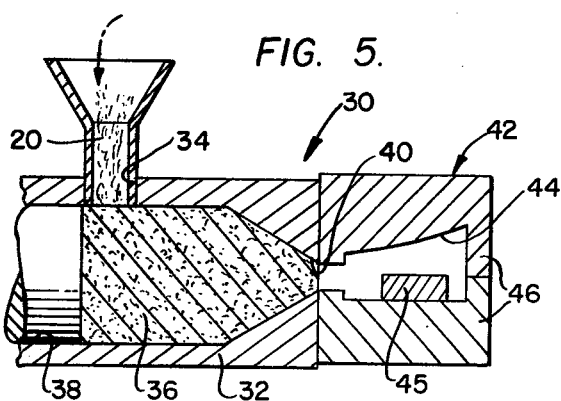
FIG. 5 is a diagrammatic view of a process step in a second novel and improved method embodying the principles of the present invention which view depicts a repulverized dental porcelain mixture with binder being charged into a mold cavity.
Figure 6:
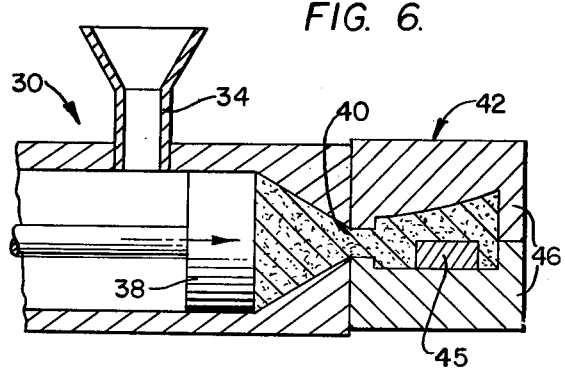
FIG. 6 is a diagrammatic view depicting the repulverized porcelain mixture with binder of FIG. 5 being injected under pressure into a suitable mold to form a suitable compressed molded product.
Figure 7:
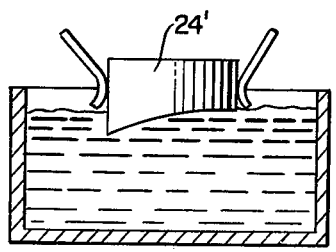
FIG. 7 represents a diagrammatic view of another process step as embodied by the second method depicted in FIGS. 5 and 6, wherein the compressed molded product is seen being dipped into a slurry of suitable occlusal or incisal dental porcelain material.

Reference is now made to FIGS. 5 to 7 to illustrate another unique and improved multi-step process involved in the manufacturing of semi-finished prosthetic dental preforms 10, such as shown in FIG. 4A. One difference between these steps and those earlier described is that an injection molding type process is utilized to mold the green or molded compact member 24' (FIG. 7) as opposed to compression molding. As with the previous embodiment, this particular method also contemplates utilization of repulverized dental porcelain 20 including a particular binder material. As will be subsequently described the novel binder of the present invention also serves as a plasticizer and lubricant. The spray dried porcelain contemplated is formed by any conventional spray drying apparatus. The resulting spray dried material with binder is, in any suitable fashion, introduced into any standard type of injection molding assembly 30. It is, of course, understood that the illustrated embodiment of the injection molding assembly 30 is only for purposes of illustration and not limitation.

As shown, the injection molding assembly 30 includes a housing member 32 with a feed opening 34 through which the spray dried repulverized material 20 is introduced into charging chamber 36 so as to fill the latter. An axially slidable movable ram 38 positioned within chamber 36 for reciprocatory movement serves to force the repulverized material 20 through outlet opening 40. As is customary in an injection molding operation a plasticizer is used in the injection molding process. It is noted the prior art plasticizers for use in injection molding ceramic materials did not completely burn out. While presence of certain amounts of plasticizer after burn out does not significantly adversely affect the injection molding of prior art products, such as spark plugs described in U.S. Pat. No. 2,964,245, it does pose appreciable drawbacks if dental preforms are to be manufactured since incomplete burn out adversely affects the desired colors.

As noted, the binder used in this particular embodiment uniquely also serves as a plasticizer and lubricant. Such binder completely burns out. As a consequence thereof, the color of dental preform 10 will not be undesirably tinted by the plasticizer.

The binder or plasticizer preferred by the present invention is a non-water soluble material with low volatility and a low melting point so as to burn out easily and completely without leaving residue which adversely affects the color.

Such plasticizer in a preferred embodiment may be generally comprised of by percentage weight 10.5% EVA (Ethylene Vinyl Acetate) resin, 5.3% mineral seal oil, and 2.2% Sterotex (i.e. synthesized stearic acid made out of hydrogenated vegetable oil) whenever there is approximately 82% body ceramic powder. Such plasticizer may also be comprised of approximately 8.5% EVA resin, 3.9% mineral seal oil, and 1.60% Sterotex whenever there is about 86% body ceramic powder. Alternatively, a plasticizer may be used having the following constitutents: 9% EVA resin, 4.2% mineral seal oil and 1.8% Sterotex whenever there is about 85% body ceramic powder. It should be understood that EVA resin and Sterotex are commercially available materials. Also, in typical fashion the die assembly 30 is heated to preheat the material within the chamber 36.

Situated immediately adjacent cavity opening 40 is an appropriate mold apparatus 42 which may include a cavity 44 defined by separable molding halves 46 and a die member 45, the latter of which is appropriately situated within the former in any suitable fashion for well known purposes and does not form an aspect of this invention. The cavity 44 has a configuration which is generally complementary to the exterior shape of the compressed green compact member 24'.

Reference is now made to FIG. 6 for purposes of illustrating the injection molding process. As depicted therein, the movable ram 38 is displaced rightwardly as shown in the drawing, to correspondingly force the repulverized dental porcelain 20 together with the noted plasticizer into the cavity 44 under sufficient pressure to mold the repulverized material. It will also be recognized, of course, that the mold cavity 44 can have other desired configurations.

The injection molding step is performed under suitable temperature and pressure conditions for the necessary duration. Since these factors are well known in the art a detailed description thereof is believed unnecessary. It will be noted that the plasticizer is completely burned off during a succeeding step leaving only the dental porcelain ceramic material in a concretious state.

At the conclusion of the foregoing injection molding step, the molding products 24' is appropriately removed from mold apparatus 42. The molded product 24' may be coated with an incisal or occlusal dental porcelain. If a subsequent outer coating is desired such is accomplished by suitable dipping into a slurry of either the incisal or occlusal dental porcelain. This procedure is shown in FIG. 7. As in the other embodiment, the green compact may be dipped into a suitable slurry and allowed to dry for several times so that the desired thickness of incisal or occlusal dental porcelain on selected surfaces can be attained. Accordingly, the appropriate incisal or occlusal porcelain is added. Beyond the dipping procedure disclosed, this embodiment may have the incisal or occlusal dental porcelain material 20 selectively applied to the surfaces of the green compact member 24' in a predetermined thickness through the other conventional steps such as immersing, spraying or brushing.

Another approach within the ambit of the invention avoids the subsequent dipping step by injection molding either incisal or occlusal dental porcelain into compact state in the cavity 44. Toward that end incisal or occlusal dental porcelain with the noted binder is introduced into the injection molding chamber. The resultant product will have a so-called incisal or occlusal color whenever such dental porcelain is used. The incisal or occlusal porcelain is injection molded under proper conditions so as to have surfaces with the desired translucent properties. A suitable gingival color can be appropriately added later filling in under the preform to form the margin. In this manner there is no need for a subsequent dipping step although such may be provided.

The molded compact dental porcelain member 24' may be suitably heated to an appropriate temperature ranging from about 200° F. to about 1200° F. or over. It is also to be understood that the heating is carried out to burn out the binder. As a consequence of the foregoing, it will be appreciated that there results a semi-finished dental porcelain prosthetic preform 10 similar to FIG. 4A which is ready for mounting on a member which forms a component of a dental appliance. On the other hand, the preform 10, as is, can be used for well known purposes.

Specific reference is now made to FIGS. 8 through 10 wherein there is depicted another sequence of operations performed by another method which is in accordance with the principles of the present invention. As with the other previously described methods, there is disclosed a process for producing semi-finished dental porcelain prosthetic preforms 50 (FIG. 8A) which may in this embodiment be a dental crown or the like.

In the illustrated embodiment, there is shown a molding apparatus 52 which facilitates the performance of the present method. The molding apparatus 52 includes a generally annular shaped outer container member 54 made of a suitable metallic material and having a stem or nipple portion 56 protruding from the closed end thereof. The stem portion 56 has an axial fluid passage 58 therethrough which, as is best shown in FIG. 9, cooperates with a conduit 60 leading to a suitable source of vacuum (not shown) for purposes afterwards made clear.

The molding apparatus 52 of this embodiment includes a generally solid and dense porous material 62 suitably compacted within the container member 54. The porous material 62 tends to be permeable to the extent it can accelerate liquid absorption. Any suitable type of porous material is contemplated within the spirit and scope of the invention. As a result of the porosity, the porous material 62 provides for a denser product relatively free of bubbles or voids which customarily result from evaporation of water during the subsequent heating.

With reference to FIG. 9, there is disclosed a protruding upwardly extending form 64 on the exposed surface of the material 62. The form 64 generally has a configuration which would be complementary to the interior surface of a semi-finished prosthetic tooth crown 50 which is sought to be produced in accordance with this particular invention. The porous form 64, as noted, is in the shape of the exterior of a tooth crown reduced by the desired dental porcelain thickness and adjusted for expected shrinkage of the dental porcelain.

Now with reference to FIG. 8, it will be noted that this particular method includes a first coating step of dipping the porous form into a container 66 holding a thin slurry containing an appropriate dental porcelain 70 having a binder therefor. Each dipping step is followed by an appropriate drying step. Such series of dipping and drying steps are performed until the desired thickness of dental porcelain 70 is achieved. It should be pointed out, however, that such thickness may be preselected to take into account such factors as shrinkage which occurs with the dental porcelain.

As shown in FIG. 9, the molding apparatus 52 is suitably connected to a suitable vacuum source (not shown) through conduit 60. By subjecting the soft dental porcelain material 70 to at least a partial vacuum or reduced pressure with respect to ambient there has been determined to be a relatively rapid evaporation of excess liquid binder and water solution during the drying of the dental porcelain to thereby achieve an even denser product free of bubbles or voids. It should be understood that the reduced pressure is in relation to the pressure surrounding the exterior of the form 64 and soft dental porcelain material. Since the partial vacuum is applied to the interior of the porous material 62 such reduced pressure enhances evaporation. By virtue of such operation the compact dental tooth crown form 72, as noted, is much denser since it is free of air bubbles and voids. As a result thereof a green type of dental crown compact 72 is formed.

Although dipping has been presently described as one manner of coating the protruding porous form 64 with a suitable dental porcelain material it is understood that other types of methods for coating are envisioned for use.

With continued reference to the present embodiment reference is made to FIG. 10 wherein there is depicted an outer dental porcelain coating step. The outer coating step follows the partial drying step utilizing the partial vacuum or reduced pressure relative to ambient pressures. As viewed the molded green tooth crown 72 is appropriately dipped into a thin slurry containing either occlusal or incisal dental porcelain material 74. As a result thereof, selected outer surfaces 75 of the compact tooth crown 72 are appropriately coated for well known purposes, such as achieving certain sizes, color and translucency. The particular achievement of such sizes, color and translucency do not form an essential aspect of this invention since their attainment is relatively well known.

As with the other dipping steps, each dipping and accompanying drying step is repeated until the desired incisal or occlusal dental porcelain thickness is attained.

The expected dental porcelain shrinkage is taken into account. Other suitable dental porcelain coating steps are, of course, envisioned for use in applying the outer coating to attain the desired color and translucency and other known properties associated with this dental porcelain coating step. Also while a single container member 54 has been disclosed, it will be understood that other arrangements providing for the formation of multiple tooth crowns are also contemplated.

To remove the prosthetic tooth crown 50, it is within the spirit of this invention to have the stem portion 56 connected to a suitable source of pressurized fluid so that such fluid pressure may upwardly force such tooth crown from the porous form 64. As a consequence of the foregoing approach there is advantageously facilitated a removal of the crown 50. Such removal occurs without significant mechanical handling hardships and, importantly, without breakage of such crowns especially insofar as the latter are relatively weak. Should other techniques be applied in order to remove the crowns there results a significant tendency for the crown to be subject to breakage.

It will be appreciated from the foregoing considerations, that by virtue of the above procedures a semi-finished prosthetic tooth crown 50 is formed which is much more rigid, and, of course, significantly stronger by virtue of the vacuuming procedure enhancing the density of the compact tooth crown 72. This particular method also includes the steps whereby the compact product is heated to approximately 400° F. and thereafter baked at a temperature of 1200° F. or above. Although the foregoing upper temperature limit can be surpassed, such temperature should not vitrify the material. In the foregoing process, the binder material, in customary fashion, is burned off.

With specific reference to the fourth method depicted in the drawing reference is made to FIGS. 11 to 14. Since the molding apparatus of this embodiment is structurally similar to the earlier described embodiment, the same reference numerals will be utilized to identify the same structure with, however, the addition of a prime marking. One of the major differences between this approach and the one earlier described is the fact that there is a recess or cavity 76 formed in the hard porous material 62' as opposed to the molded form 64 of the earlier described embodiment. As with the other embodiment, the hard porous material 62' is made from any suitable and conventional type of permeable material which can be used in the molding process contemplated by the present method. As indicated, the porous character of the material 62' draws off excess liquid by capillary action providing a denser product free of the bubbles or voids resulting from evaporation of liquid binder and water solution during subsequent heating. In connection with the cavity or recess 76, such has a configuration which is generally similar to the exterior surface of molded tooth crown 50 (FIG. 8A) which is to be formed by this process. Of course, the recess 76 may have any size, shape or contour and be able to withstand the temperature involved without failure.

In connection with FIG. 11, there is shown the pouring step of this particular method. It will be understood that a slurry 78 of dental porcelain material is first poured into the cavity 76. After the dental porcelain slurry mixture has been poured, the molding apparatus 52' is conveniently moved and, preferably, rotated so that the movement forces generated tend to generally uniformly distribute and increase the thickness of the walls of the tooth crown compact 80 to be formed. Such apparatus 52' is rotated until a predetermined wall thickness of porcelain is attained within the cavity. It should be understood, of course, that during this step the liquid absorption characteristics of the porous material 62' draws off excess liquid from the slurry. The desired thickness will take into account, of course, the expected dental porcelain shrinkage. At the conclusion of the step involving the forming of the tooth crown member 80, the excess dental porcelain slurry 78 is poured out. It will be appreciated that the wall is formed as a result of the slurry drying upon exposure to the porous material.

As shown in FIG. 12 the green tooth crown 80, while still relatively soft is subject to at least a partial vacuum or reduced pressure with respect to ambient. As in the other embodiment, the partial vacuum tends to increase evaporation of excess liquid through the material 62' especially from the intended exterior surface of the tooth crown compact 80. Such vacuum besides facilitating evaporation of the liquid binder and water solution improves the density of the tooth crown 80 since it serves to further reduce air bubbles and voids forming in the latter.

To remove the dried dental tooth crown compact 80 after the preselected dental porcelain thickness has been attained, this invention envisions that air travelling through conduit 60' and material 62', at a suitable pressure level, forces the tooth crown compact from the recess 76. Accordingly, the removal operation is achieved in an advantageous and nondestructive fashion.

After the removal step occurs then there is contemplated an outer coating step, wherein incisal or occlusal dental porcelain material may be applied to selected surfaces, in any suitable fashion. Such additional coating of dental incisal or occlusal porcelain may be applied through other suitable and equivalent coating approaches, such as immersing, spraying and brushing. Whatever coating step is employed, however, it will be appropriately performed to apply the proper thickness of either incisal or occlusal dental porcelain taking into account and compensating for expected shrinkage of such porcelain during drying.

Although not shown in this embodiment, it will be understood that the molded tooth crown, which is formed by virtue of the foregoing steps depicted in FIGS. 11 to 14, may be suitably and conventionally heated to approximately 400° F. and, thereafter, baked at a temperature of about 1200° F. or over, provided that the material is not vitrified since other difficulties would arise such as the binder not being able to completely burn out and it would be hard to mold the surfaces. Suitable apparatus is contemplated for doing such heating and baking. Accordingly, the binder material will be completely burned off.

It will be understood that incisal or occlusal dental porcelain are actually comprised of the same dental porcelain material. As used in the dental field occlusal or incisal dental porcelain actually refers to the particular locations on the prosthetic member the material will be deposited on. The incisal or occlusal dental porcelain is, of course, to be contrasted with what is referred to as body or gingival dental porcelain. Generally, the dental porcelain which is to be repulverized is of the body type, although this invention also encompasses that so-called incisal or occlusal dental porcelain can be repulverized.

After having described the aforenoted methods for forming semi-finished tooth components, it is believed quite evident that there can be produced a significantly enhanced manufacturing of such semi-finished dental preforms in a manner whereby there is greater accuracy, particularly from the standpoint of mass production of these prosthetic preforms such as crowns.

While the invention has been described in connection with the preferred embodiments, it is not intended to limit the invention to the particular form set forth above, but, on the contrary, it is intended to cover such alternatives, modifications and equivalents as may be included within the spirit and scope of the invention as defined by the appended claims.

What is claimed is:

1. A method for producing semi-finished prosthetic dental preforms consisting essentially of repulverizing a dental porcelain mixture including a suitable binder material which also serves as a plasticizer and lubricant by spray drying such dental porcelain mixture, molding the repulverized dental porcelain mixture in a mold member having a cavity with a form generally complementary to that desired for the molded product, removing the molded product from the mold; and applying an outer coating of incisal or occlusal dental porcelain to selected exterior surfaces of the molded product and heating and baking the molded product until said binder is completely burned out and until the molded product becomes a hard concretious material, said binder comprising between about 14 to 18% by weight of the dental porcelain mixture and including about between 10.5% to 8.5% EVA resin, 5.3% to 3.9% mineral seal oil and about 2.2% to 1.6% stearic acid.

2. The method of claim 1 wherein pressurized fluid is applied to the molded product so as to enable lifting and removal of the molded product from the mold member.

3. A method for producing semi-finished prosthetic dental preforms consisting essentially of repulverizing occlusal or incisal dental porcelain including a suitable binder material which also serves as a plasticizer and lubricant by spray drying such dental porcelain, molding the repulverized dental porcelain mixture in a mold member having a cavity with a form generally complementary to that desired for the molded product, removing the molded product from the mold, and heating and baking the molded product until said binder is completely burned out and until the molded product becomes a hard concretious material, said binder comprising between about 14 to 18% by weight of the dental porcelain mixture and including about between 10.5% to 8.5% EVA resin, 5.3% to 3.9% mineral seal oil and about 2.2% to 1.6% stearic acid.

4. The method of claim 3 wherein said removal step comprises applying pressurized fluid to the molded article to facilitate lifting and removal of the molded article from the cavity.

* * * * *